United States Patent
Rabizadeh et al.

(10) Patent No.: US 10,323,285 B2
(45) Date of Patent: Jun. 18, 2019

(54) PROTEOMICS ANALYSIS AND DISCOVERY THROUGH DNA AND RNA SEQUENCING, SYSTEMS AND METHODS

(71) Applicant: Nantomics, LLC, Culver City, CA (US)

(72) Inventors: Shahrooz Rabizadeh, Los Angeles, CA (US); Patrick Soon-Shiong, Culver City, CA (US); Stephen Charles Benz, Santa Cruz, CA (US)

(73) Assignee: NANTOMICS, LLC, Culver City, CA (US)

( * ) Notice: Subject to any disclaimer, the term of this patent is extended or adjusted under 35 U.S.C. 154(b) by 365 days.

(21) Appl. No.: 14/917,945

(22) PCT Filed: Sep. 9, 2014

(86) PCT No.: PCT/US2014/054849
§ 371 (c)(1),
(2) Date: Mar. 9, 2016

(87) PCT Pub. No.: WO2015/035415
PCT Pub. Date: Mar. 12, 2015

(65) Prior Publication Data
US 2016/0215350 A1     Jul. 28, 2016

Related U.S. Application Data

(60) Provisional application No. 61/875,583, filed on Sep. 9, 2013.

(51) Int. Cl.
*C07H 21/04* (2006.01)
*C12Q 1/68* (2018.01)
*C12Q 1/6886* (2018.01)
*G06F 19/22* (2011.01)

(52) U.S. Cl.
CPC ........... *C12Q 1/6886* (2013.01); *G06F 19/22* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

PUBLICATIONS

Hernandez et al. Clinical Cancer Research, vol. 11, No. 15, pp. 5444-5450 (Year: 2005).*
Hodgson et al. (Technical Briefs, vol. 47, No. 4, pp. 774-778, 2001) (Year: 2001).*
Schilichtholz et al (Carcinogenesis, vol. 25, No. 12, pp. 22319-22323, 2004). (Year: 2004).*

* cited by examiner

*Primary Examiner* — Jeanine A Goldberg
(74) *Attorney, Agent, or Firm* — Umberg / Zipser, LLP

(57) ABSTRACT

Specific mutations of FGFR3 (S249C) and of TP53 (V272M) are identified as being characteristic of breast cancer, and of having utility in diagnosis and prognosis of an individual with breast cancer. Systems and methods useful for identification of such mutations are also presented.

9 Claims, 1 Drawing Sheet

| Gene | Mutation Type | DbSNP Marker | Known Cancer Gene | Cosmic % | Protein Change | Genomic Position | Ref | Alt | Total Depth | Alt Allele Depth | Alt Allele % |
|---|---|---|---|---|---|---|---|---|---|---|---|
| FGFR3 | Missense | | Yes | 53.70% | p.S249C | chr4:1803568 | C | G | 1,608 | 642 | 39.90% |
| KDR | Silent | rs35961234 | Yes | 3.40% | | chr4:55946171 | G | A | 808 | 518 | 64.10% |
| APC | Frame Shift Ins | | Yes | 2.80% | | chr5:112175951 | G | GA | 1,254 | 131 | 10.40% |
| FBXW7 | Frame Shift Del | | Yes | 1.50% | | chr4:153249360 | CT | C | 1,068 | 946 | 28.60% |
| TP53 | Missense | | Yes | 0.60% | p.V272M | chr17:7577124 | C | T | 834 | 739 | 88.60% |
| PDGFRA | Silent | rs1873778 | Yes | 0.50% | | chr4:55141055 | A | G | 815 | 815 | 100.00% |
| APC | Silent | rs41115 | Yes | 0.30% | | chr5:112175770 | G | A | 2,109 | 2,083 | 98.80% |
| PTEN | Frame Shift Ins | | Yes | 0.20% | | chr10:89720811 | C | CA | 255 | 47 | 18.40% |
| TP53 | Frame Shift Del | | Yes | 0.10% | | chr17:7578474 | CG | C | 757 | 682 | 90.10% |
| TP53 | Missense | rs1042522 | Yes | 0.00% | p.P72R | chr17:7579472 | G | C | 405 | 395 | 97.50% |
| FGFR3 | Silent | rs7688609 | Yes | 0.00% | | chr4:1807894 | G | A | 1,850 | 1,841 | 99.50% |
| RET | Silent | rs1800861 | Yes | 0.00% | | chr10:43613843 | G | T | 1,772 | 1,759 | 99.30% |
| KDR | Frame Shift Del | | Yes | 0.00% | | chr4:55955084 | GA | G | 4,026 | 3,833 | 95.20% |
| IDH2 | Frame Shift Del | | Yes | 0.00% | | chr15:90631885 | GT | G | 1,486 | 1,412 | 95.00% |
| STK11 | Frame Shift Del | | Yes | 0.00% | | chr19:1221313 | AG | A | 2,508 | 2,377 | 94.80% |
| MET | Frame Shift Del | | Yes | 0.00% | | chr7:116411959 | AG | A | 1,195 | 1,113 | 93.10% |
| HRAS | Frame Shift Del | | Yes | 0.00% | | chr11:534293 | GC | G | 900 | 809 | 89.90% |
| IDH1 | Frame Shift Del | | Yes | 0.00% | | chr2:209113159 | AT | A | 3,317 | 2,959 | 89.20% |
| IDH2 | Frame Shift Del | | Yes | 0.00% | | chr15:90631917 | TC | T | 1,496 | 1,330 | 88.90% |
| KIT | Frame Shift Del | | Yes | 0.00% | | chr4:55595549 | AT | A | 2,063 | 1,819 | 88.20% |
| HRAS | Silent | rs12628 | Yes | 0.00% | | chr11:534242 | A | G | 905 | 794 | 87.70% |
| JAK2 | Missense | | Yes | 0.00% | p.M601R | chr9:5073723 | T | G | 40 | 35 | 87.50% |
| SMAD4 | Frame Shift Del | | No | 0.00% | | chr18:48584553 | AG | A | 446 | 343 | 76.90% |
| RET | Silent | rs1800863 | Yes | 0.00% | | chr10:43615633 | C | G | 855 | 449 | 52.50% |
| PTEN | Missense | | Yes | 0.00% | p.H61Y | chr10:89685286 | C | T | 339 | 56 | 16.50% |
| KIT | Frame Shift Ins | | Yes | 0.00% | | chr4:55602700 | A | AT | 4,181 | 578 | 13.80% |
| EGFR | Silent | rs1050171 | Yes | 0.00% | | chr7:55249063 | G | A | 278 | 33 | 11.90% |

PROTEOMICS ANALYSIS AND DISCOVERY THROUGH DNA AND RNA SEQUENCING, SYSTEMS AND METHODS

This application claims the benefit of U.S. Provisional Application No. 61/875,583 filed on Sep. 9, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is proteomic analysis, more particularly proteomic analysis through genetic sequencing.

BACKGROUND

The following description includes information that may be useful in understanding the present invention. It is not an admission that any of the information provided herein is prior art or relevant to the presently claimed invention, or that any publication specifically or implicitly referenced is prior art.

Breast cancer, as the name implies, refers to cancers that form in breast tissue, primarily in milk ducts and lobules. Although rare in males, it can occur in either gender. It is the most common form of cancer in women and is second only to lung cancer in terms of fatality. While breast cancer rates have been decreasing since 2000 it is estimated that approximately 1 in 8 women in the United States will develop invasive breast cancer. Approximately 5% to 10% of breast cancers are thought to be linked to inherited genetic mutations, the most well known being mutations to the BRCA1 and BRCA2 genes. The majority of breast cancers do not appear to be associated with inherited mutations, and are thought to be due to mutations that occur due to aging and environmental exposure.

Currently breast cancer is diagnosed by imaging and cytology of biopsied specimens, which usually follows from abnormal findings from self examination or from screening (for example, mammograms, breast MRI, and breast ultrasound examination). Such methods, however, may not provide complete information regarding prognosis, what treatment modalities may be more effective, and the likelihood of reoccurrence.

More recently approaches have been developed that utilize mutation analysis to more accurately identify cancerous or neoplastic cells and to provide a more complete clinical picture for the physician. Such approaches can address inherited mutations (for example, BRCA1 and BRCA2), but can also address mutations acquired through aging and environmental exposure. For example, United States Patent Application US 2010/0,255,470 (to Bankaitis-Davis et al) describes the use of expression profiling of TP53 for the characterization of suspected neoplastic cells. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Similarly, European Patent Application 2,083,088A2 (to Lai and Fanidi) discusses expression profiling of TP53 and numerous other potential cancer markers for the diagnosis of breast and other cancers. Identification of specific mutations of TP53 have also been proposed for assessing susceptibility to breast cancer (United States Patent Application 2011/0,015,081, to Stacey et al). TP53 is mutated in approximately 50% of cancers, however, so while characterization of this gene may have utility it may lack specificity.

Specificity can potentially be improved by characterizing more than one genetic marker. For example, International Patent Application 2013/075059 A1 (to Pietenpol) discusses characterization of the expression profiles of groups of genetic markers in the characterization of breast cancer. United States Patent Application 2014/0,121,128 (to del Sal et al) discusses characterization of a specific TP53 variant in combination with expression profiling of 10 ore other genes for determining the prognosis of a person with breast cancer. Similarly, International Patent Application 2012/092,426 A1 (to Downing et al) and International Patent Application 2014/004,726 A1 (to Chen et al) discuss identifying 20 or more specific mutations, including mutations in TP53, to diagnose or otherwise characterize a variety of cancers, including breast cancer. United States Patent Application 2013/0,143,747 (to Gutin et al) discusses the use of information from the Catalogue of Somatic Mutations in Cancer to identify specific mutations of TP53 that can be used in combination with specific mutations of APC, KRAS, BRAF, and EGFR in the diagnosis of various cancers, including breast cancer.

Such approaches, however, have their shortcomings. Expression profiling, for example, requires accurate quantitation of the gene product (i.e. RNA), which in turn involves accurate reverse transcription and amplification to provide useful data. Such accurate quantitation can be difficult to achieve, particularly from clinical specimens. Accurate identification of numerous specific mutations carries similar risks, particularly where an erroneous individual result can impact the analysis.

Thus, there is still a need for a method of characterizing a sample from a breast cancer or other cancer using a limited number of genetic markers, and for a method of identifying such markers.

SUMMARY OF THE INVENTION

The inventive subject matter provides apparatus, systems and methods in which a plurality of genetic markers are identified by sequencing of DNA, RNA, and/or cDNA obtained from a sample, and associated with a tumor or neoplasm by comparison to a catalog of known mutations and their frequency of association with neoplasms. In particular a specific mutation in FGFR3 and a specific mutation in TP53 and their association with breast cancer is identified. This association can be determined without comparison of such sequence data to sequences derived from non-neoplastic tissue, in particular non-neoplastic tissue from the same subject. Such a plurality of markers can have diagnostic and/or prognostic utility in diagnostic applications for tumor or neoplasm identification or susceptibility.

One embodiment of the inventive concept is a method of identifying an individual that is susceptible to breast cancer by obtaining a tissue sample from the individual, performing a genetic analysis, and identifying mutations in the FGFR3 gene at the position corresponding to amino acid 249 and at the position in the TP53 gene corresponding to amino acid 272. This identification is made without reference to a second tissue sample taken from the individual. The genomic analysis can be a sequence analysis of genomic DNA, mRNA, and/or a cDNA transcript of mRNA from which at least one intron has been excised. In a preferred embodiment of the inventive concept, the FGFR3 mutation is an S249C mutation. In another preferred embodiment the TP53 mutation is a V272M mutation. Identification of both of these genetic markers indicates that the individual has developed and/or is susceptible to developing breast cancer.

Another embodiment of the inventive concept is a method of identifying a tissue sample as having originated from a breast cancer or neoplasm. A tissue sample is obtained from the suspect tissue of an individual, and a genetic analysis is performed. The genomic analysis can be a sequence analysis of genomic DNA, mRNA, and/or a cDNA transcript of mRNA from which at least one intron has been excised. The genetic analysis is performed without reference to a different and/or normal tissue of the same individual. The sites in the FGFR3 gene at the position corresponding to amino acid 249 and at the position in the TP53 gene corresponding to amino acid 272 are characterized and analyzed for mutations. In a preferred embodiment of the inventive concept, the FGFR3 is an S249C mutation. In another preferred embodiment the TP53 mutation is a V272M mutation.

Another embodiment of the inventive concept is a method of identifying a plurality of tumor markers, in which a sample is obtained from a neoplasm and sequence data is obtained by genomic analysis. The genomic analysis can be a sequence analysis of genomic DNA, mRNA, and/or a cDNA transcript of mRNA from which at least one intron has been excised. The sequence data is compared to a sequence catalog (for example, COSMIC) that includes frequency data related to the frequency with which specific mutations are associated with neoplasms or neoplastic disease. This comparison is used to identify mutation sites in the sequence data that correspond to a frequency of association of 0.6% or greater. The genomic analysis can be performed without reference to samples obtained from non-neoplastic sources. In a preferred embodiment of the inventive concept, the plurality of tumor markers has at least first and second tumor markers. For example, genomic analysis of a sample of tissue from a breast cancer can provide sequence data that shows a mutation at the position corresponding to amino acid 272 in TP53 and a mutation at the position corresponding to amino acid 249 in FGFR3 are both present.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWINGS

FIG. 1 depicts a set of genetic mutations identified in a sample obtained from a breast neoplasm, with comparison to the frequency with which the genetic mutation is associated with neoplasm as recorded in the Catalogue of Somatic Mutations in Cancer.

DETAILED DESCRIPTION

The inventive subject matter provides apparatus, systems and methods in which a plurality of genetic markers are identified by sequencing of DNA, RNA, and/or cDNA obtained from a sample, and associated with a tumor or neoplasm by comparison to a catalog of known mutations and their frequency of association with neoplasms. In particular, such apparatus, systems, and methods have been applied to identify the S249C mutation of FGFR3 and the V272M mutation of TP53 as having particular utility in the characterization of breast cancer. For the purposes of this application, samples taken from neoplastic tissues can be understood to include samples taken from a neoplasm of an individual or to include cells obtained from cell culture that were either originally derived from neoplastic tissue or that induce neoplasms when introduced to a subject. Such samples can be obtained from a patient, and can be taken from tissue suspected of being neoplastic or from apparently normal tissue. This association of genetic data with neoplasticity can be determined without comparison of sequence data to sequences derived from non-neoplastic tissue, in particular non-neoplastic tissue from the same subject.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Once identified, the association of specific combinations of mutations can have diagnostic and/or prognostic utility in diagnostic applications for tumor or neoplasm identification or susceptibility. In particular a specific mutation in FGFR3 in combination with a specific mutation in TP53 can be identified through their association with breast cancer as indicative of a particular tissue sample being a obtained from a breast cancer, the presence of a subclinical (i.e. microscopic) neoplasm in apparently normal tissue, and/or the identification of an individual as being susceptible to the development of breast cancer. In a preferred embodiment of the inventive concept, an S249C mutation of FGFR3 in combination with a V272M mutation of TP53 is indicative of the presence of breast cancer, and has utility in diagnostic and/or prognostic applications.

One embodiment of the inventive concept is a method of identifying a plurality of tumor markers that are associated with a neoplasm. These tumor markers can be specific mutations (for example, deletions, duplications, frame shifts, and/or missense mutations) in genes associated with expressed proteins. As such, they can be detected by genomic analysis. In some embodiments this can be performed by analysis of genomic DNA and/or of mRNA isolated from a sample taken from a neoplasm. In a preferred embodiment, the genomic analysis is a sequence analysis of cDNA derived from mRNA from which at least one intron has been excised. In such a genetic analysis a sequence of the transcriptome, or a portion thereof, is obtained. Such a genetic analysis, which provides data related to expressed proteins, can provide information related to processes that are more directly related to tumorigenesis and other neoplastic phenomena than a strictly genomic approach.

Genomic analysis can be performed by any suitable method, including rapid or "next generation" sequencing techniques that provide high resolution information over the entire sequence. It is contemplated, however, that such sequence analysis can be performed by SNP characterization, for example by single base extension followed by high resolution separation and/or hybridization to a suitable microarray.

Once obtained, sequence data can be characterized by comparison to a sequence database or catalog (for example, COSMIC) that includes frequency data related to the frequency with which specific mutations are associated with neoplasms or neoplastic disease. Determination that mutations identified in the sample are present in such a database and associated with neoplastic tissue or neoplastic disease at a rate exceeding a threshold value can cause these mutations to be identified as a tumor marker associated, when present in combination, with the tumor type from which the sample was derived. Suitable threshold values can be 0.1% 0.2%, 0.3%, 0.4%, 0.5%, 0.6% 0.7%, 0.8%. 0.9%, 1.0%, or greater. In a preferred embodiment the threshold value is equal to or greater than 0.5%. In an especially preferred embodiment the threshold value is equal to or greater than 0.6%.

It should be appreciated that this methodology is particularly suited to identification of combinations of known tumor markers as indicators of neoplastic diseases (or susceptibility to neoplastic diseases) in combination that they are not associated with individually. As such, this method advantageously provides tumor marker sets that provide a higher degree of accuracy and/or sensitivity in determining the neoplastic status of a tissue sample than the conventional use of single tumor markers. In addition, by avoiding reliance on comparison to "normal" tissue, this method advantageously utilizes a single genomic characterization step, vastly reducing time and expense.

In an example of the implementation of such a method, a sample was obtained from breast cancer tissue of an afflicted individual. Genetic analysis of the sample was performed without comparison to results from normal tissue. As shown in FIG. 1, the analysis revealed a number of apparently somatic mutations. Comparison of these mutations with the Catalogue of Somatic Mutations in Cancer (COSMIC) database, which includes mutations in known cancer-related genes that are collected from the scientific literature and data collected from whole genome sequencing studies performed as part of the Cancer Genome Project, was performed. Application of a threshold value of 0.6% applied to the frequency with which the observed mutations were reported within the database revealed that two of these, S249C in FGFR3 and V272M in TP53 are, in combination, an indicator of breast cancer. It should be appreciated that, prior to these findings, FGFR3 was not associated with breast cancer, but rather with urinary tract cancers (see European Patent 1,208,231 B2, to Cappellen et al; United States Patent Application 2013/0,059,303, to Radvany; and International Patent Application 2009/036,922 to Renard and Van Criekinge).

Another embodiment of the inventive concept is a method of identifying an individual that is susceptible to breast cancer. In such a method a tissue sample is obtained from the individual for genetic analysis. Such a sample can be obtained from breast or breast-associated tissue, from a suspect lesion, or from an unrelated tissue (for example, blood). DNA, RNA, and/or cDNA obtained by reverse transcription of mRNA to provide a reverse transcript from which at least one intron has been excised is amplified and subjected to genetic analysis. Such genetic analysis can be performed by any suitable technology, including "next generation" high throughput sequencing that provides a detailed genetic sequence of the entire genome and/or transcriptome presented.

This detailed genetic sequence can then be reviewed or otherwise evaluated for the presence of a plurality of genetic markers identified as related to breast cancer when observed simultaneously, for example mutations at the position in the FGFR3 gene corresponding to amino acid 249 and at the position in the TP53 gene corresponding to amino acid 272. In a preferred embodiment, these mutations correspond to S249C in FGFR3 and V272M in TP53 and can be made without reference to a second tissue sample taken from the individual. Alternatively, SNP analysis can be performed to determine the identity of mutations at predetermined locations in the genome and/or transcriptome. SNP analysis can be performed by any suitable method, for example single base extension of synthetic primers prepared against regions immediately adjacent to the mutation site, followed by high resolution separation or hybridization to a microarray. Such SNP analysis can utilize a multiplex format that simultaneously identifies all mutations identified as relevant to breast cancer and/or breast cancer susceptibility simultaneously.

Another embodiment of the inventive concept is a method of identifying a tissue sample or cell line as having originated from a breast cancer or neoplasm. A tissue sample can be obtained from the suspect tissue of an individual, from a metastatic site, or from cells isolated from circulation (for example, via cell sorting). Cells from cell lines can be obtained from cell culture or from lesions developing following implantation into test animals (for example, from a xenograft into a nude mouse). DNA, RNA, and/or cDNA obtained by reverse transcription of mRNA to provide a reverse transcript from which at least one intron has been excised is amplified and subjected to genetic analysis. Such genetic analysis can be performed by any suitable technology, including "next generation" high throughput sequencing that provides a detailed genetic sequence of the entire genome and/or transcriptome presented.

This detailed genetic sequence can then be reviewed or otherwise evaluated for the presence of a plurality of genetic markers identified as related to breast cancer when observed simultaneously, for example mutations at the position in the FGFR3 gene corresponding to amino acid 249 and at the position in the TP53 gene corresponding to amino acid 272. In a preferred embodiment, these mutations correspond to S249C in FGFR3 and V272M in TP53 and can be made without reference to a second tissue sample taken from the individual. Alternatively, SNP analysis can be performed to determine the identity of mutations at predetermined locations in the genome and/or transcriptome. SNP analysis can be performed by any suitable method, for example single base extension of synthetic primers prepared against regions immediately adjacent to the mutation site, followed by high resolution separation or hybridization to a microarray. Such SNP analysis can utilize a multiplex format that simultaneously identifies all mutations identified as relevant to breast cancer and/or breast cancer susceptibility simultaneously.

Another embodiment of the inventive concept is a marker identification system that can be utilized to identify a plurality of mutations associated with a neoplasm. Such a system can include an isolation engine, which serves to treat tissue and/or cellular samples in order to isolate nucleic acids in a form suitable for amplification. Such an isolation engine can, for example, dispense reagents or perform mechanical operations (for example, sonication, expression through an orifice, or blending with beads) that release nucleic acids (i.e. DNA and/or RNA) from tissue or cells provided to the system. Such an isolation engine can also dispense reagents that separate or otherwise isolate nucleic acids from the resulting mixture, for example by precipitation or capture on a solid phase (for example a filter or suitably coated magnetic particle). Once isolated, nucleic acids can be transferred to an amplification engine.

The amplification engine can include reagents, such as synthetic primers, nucleotides, and polymerases that permit replication of all or part of the nucleic acid supplied by the isolation engine. For example, and amplification engine can include a thermal cycler and utilize random primers and a thermophilic DNA polymerase to replicate and amplify DNA from a sample of nucleic acid provided by the isolation engine. Alternatively, the amplification engine can provide a reverse transcriptase, nucleotides, and suitable primers to generate a cDNA from mRNA supplied by the isolation engine. In such an embodiment the amplification engine can then provide a DNA polymerase, nucleotides, and synthetic primers suitable for replication and amplification of the cDNA using a thermal cycler or other suitable device. In some embodiments a single enzyme can incorporate both reverse transcriptase and DNA polymerase activity.

The amplification engine, in turn, supplies amplified nucleic acids to a sequencing engine. The sequencing engine can utilize any suitable technology for extracting sequence information from the amplified nucleic acid. For example, the sequencing engine can perform massively parallel sequencing to provide a level of overreading sufficient to generate a detailed genetic sequence for essentially all (i.e. >80%) of the amplified nucleic acid sequences. Suitable high throughput sequencing methods include massively parallel signature sequencing, polony sequencing, parallelized pyrosequencing (for example 454™ sequencing from Roche Diagnostics), reversible dye terminator sequencing (for example Solexa™ sequencing from Illumina), ligation sequencing (for example SOLID™ from Life Technologies), and semi-conductor based sequencing (for example ION TORRENT from Life Technologies). Sequence data developed in the sequencing engine is then provided to the marker analysis engine.

The marker analysis engine receives sequence data related to the nucleic acids extracted from the tissue or cell sample, and compares it to comparative sequence data related to known mutations that have been associated with various neoplasms. In some embodiments of the inventive concept the marker analysis engine first identifies mutations within the sequence data by comparison to a genomic and/or transcriptomic consensus sequence. Differences noted upon alignment between the sequence data (or a portion thereof) and the consensus sequence (or a portion thereof) can be designated as sample mutations, which are then subjected to further analysis. Sample mutations can be compared to comparative sequence data stored in a database (for example, COSMIC data as described above), where such a database includes information related to specific neoplastic mutations and the frequency with which those neoplastic mutations are associated with neoplasms. In some embodiments, the database also includes information related to the tissue origin and/or type of neoplasm associated with the neoplastic mutations. Such a comparison can yield a report, which can list all mutations identified within the sequence data and include a frequency of association of such mutations with neoplastic disease (if any) as derived from correlation to neoplastic mutations stored in the database. An example of such a report is shown in FIG. 1. A frequency that meets or exceeds a designated threshold limit (for example, 0.6%) can denote a mutation that indicates that the sample was obtained from a tissue that was at least potentially neoplastic. In a preferred embodiment, two or more mutations are identified from a neoplastic tissue of known origin in order to identify a mutation panel that is indicative of the neoplastic disease associated with the tissue.

It should be appreciated that such a database may not be static, and is preferably continuously updated. In particular, mutation panel data generated through use of the marker identification system can itself be added to the database in order to further improve identification and accuracy going forward.

Another embodiment of the inventive concept is an analytical system that utilizes genomic and/or proteomic sequence data to identify neoplastic lesions or persons at risk for development of neoplastic lesions. In such a system the isolation, amplification, and sequencing engines are essentially as described above and, in fact, can share identity with them as part of a larger system that includes a marker identification system as described above. The analytical portion of the analytical engine can be similar to that of the marker identification system noted above, however the report generated correlates the mutations identified within the sample with stored data relating the combination of mutations with the origin of the neoplasms associated with the observed combination of mutations, thus providing an assessment of the tissue of origin and/or type.

Alternatively, the sequencing engine of the analytical system can identify specific mutations within the amplified nucleic acid sample, for example by SNP analysis, rather than detailed sequence data. For example, SNPs can be identified by single base extension of synthetic primers that are complementary to SNPs that are associated with neoplastic mutations that are stored in the database. Such single base extension reactions can be performed in a multiplex fashion, with the resulting single base extension products analyzed by high resolution separation or by hybridization to a planar or suspension array.

It should also be appreciated that identification of subsets of mutations in combination, in addition to improving diagnostic accuracy and sensitivity, can also indicate potential treatment modalities. For example, identifying a sample as containing the S249C FGFR3 mutation and the V272M TP53 mutation is not only indicative that the sample originated from breast cancer tissue or potential breast cancer tissue, it is also indicative that the neoplastic disease may be susceptible to agents that are known to be effective in treating FGFR3-altered neoplasms. For example, PONATINIB™ (Ariad Pharmaceuticals) has been shown to be active against FGFR3 carrying the S249C mutation and may not normally have been considered as a therapeutic modality for an individual with breast cancer. Similarly, specific subsets of mutations can be identified or associated with different prognoses or expected clinical outcomes, which can provide a clinician with guidance towards appropriate therapeutic intervention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of diagnosing and treating an individual suspected to have breast cancer, comprising:
 a) obtaining a first tissue sample from the individual suspected to have breast cancer;
 b) performing a first genomic analysis on the tissue sample;
 c) detecting a first mutation at amino acid position 249 of the FGFR3 gene and a second mutation at amino acid position 272 of the TP53 gene;
 d) diagnosing the individual with both the mutations as having breast cancer; and
 e) treating the individual diagnosed with breast cancer with an agent known to be effective in treating FGFR3-altered neoplasm.

2. The method of claim 1, wherein the first genomic analysis is performed without reference to a second genomic analysis performed on a normal tissue sample from the individual.

3. The method of claim 1, wherein the first genomic analysis is sequencing of a cDNA prepared from an mRNA obtained from the first sample, wherein the cDNA is generated by excising at least one intron from the corresponding genomic DNA of the first sample.

4. The method of claim 1, wherein the first mutation is an S249C mutation.

5. The method of claim 1, wherein the second mutation is a V272M mutation.

6. The method of claim 1, wherein the agent is Ponatinib.

7. The method of claim 1, wherein the first genomic analysis is performed by SNP analysis.

8. The method of claim 7, wherein the SNP analysis is performed using single base extension of synthetic primers that are prepared against regions immediately adjacent to the positions in the FGFR3 gene corresponding to amino acid 249 and the position in a TP53 gene corresponding to amino acid 272.

9. The method of claim 8, wherein the SNP analysis further comprises high resolution separation or hybridization to a microarray.

* * * * *